United States Patent [19]
Holms

[11] Patent Number: 5,773,573
[45] Date of Patent: Jun. 30, 1998

[54] HIV PEPTIDES

[76] Inventor: Rupert Holms, 66 Regent's Park Road, London NWI 75X, Great Britain

[21] Appl. No.: 461,564

[22] Filed: Jun. 5, 1995

[30] Foreign Application Priority Data

Jun. 8, 1994 [GB] United Kingdom .................. 9411534

[51] Int. Cl.$^6$ .......................... A61K 38/04; A61K 39/21; A61K 39/38; C07K 5/00
[52] U.S. Cl. .......................... 530/327; 530/326; 530/325; 530/324; 424/208.1; 424/184.1; 424/188.1
[58] Field of Search .............................. 424/208.1, 188.1, 424/204.1; 530/326, 325, 324

[56] References Cited

FOREIGN PATENT DOCUMENTS

| 9200755 | 1/1992 | WIPO . |
| 9205196 | 4/1992 | WIPO . |
| 9222572 | 12/1992 | WIPO . |
| 9315750 | 8/1993 | WIPO . |
| 9403487 | 2/1994 | WIPO . |

OTHER PUBLICATIONS

Araga, S. et al. (1993) "Prevention of experimental autoimmune myasthenia gravis by manipulation of the immune network with a complementary peptide for the acetylcholine receptor" Proc. Natl. Acad. Sci. USA 90:8747–8751.

Egerton, M. et al. (1992) "Identification of Ezrin as an 81–kDa Tyrpsine–phosphorylated Protein in T Cells" The Journal of Immunology 149:1847–1852.

Krieg, J., T. Hunter (1992) "Identification of the Two Major Epidermal Growth Factor–induced Tyrosine Phosphorylation Sites in the Microvillar Core Protein Ezrin" The Journal of Biological Chemistry 267(27):19258–19265.

Briner, T.J. et al. (1993) "Peripheral T–cell tolerance induced in naive and primed mice by subcutaneous injection of peptides from the major cat allergen Fel d l" Proc. Natl. Acad. Sci. USA 90:7608–7612.

Stephen, H. et al. (1990) "Could specific oral tolerance be a therapy for autoimmune disease?" Immunology Today 11(11):396–399.

Sayegh, M.H. et al. (1992) "Induction of immunity and oral tolerance with polymorphic class II major histocompatibility complex allopeptides in the rat" Proc. Natl. Acad. Sci. USA 89:7762–7766.

Whitacre, C.C. et al. (1991) "Oral Tolerance in Experimental Autoimmune Encephalomyelitis III. Evidence for Clonal Anergy" The Journal of Immunology 147(7):2155–2163.

*Primary Examiner*—Lynette F. Smith
*Attorney, Agent, or Firm*—Salinwanchik, Lloyd & Saliwanchik

[57] ABSTRACT

It is an object of the present invention to provide preparations for the treatment or prophylaxis of AIDS and systemic lupus erythematosus and related disorders. The invention is based on the discovery of the process triggered in the immune system by HIV which leads to AIDS. HIV has a specific mechanism to activate the immune system to allow it to replicate and this same immune activation leads to an autoimmune process which eventually leads to AIDS. The preparation for treatment comprises novel synthesized peptides whose amino acid sequences are derived from a human protein called ezrin and are based on the following sequence: NH$_2$ThrGluLysLysArgArgGluThrValGluArg GluLysGluCOOH SEQ ID. No. 2. The mechanism of action of these peptides is that they switch off specific retrovirally induced immune responses by immunological tolerance.

1 Claim, 3 Drawing Sheets

HIV PEPTIDES

BACKGROUND OF THE INVENTION

The field of the present invention relates to the prevention and treatment of Acquired Immune Deficiency Syndrome (AIDS), systemic lupus erythematosus (SLE) and related diseases. As used herein, the various titles, and other such headings are intended for guidance, and should not be construed as limiting on the present invention.

Over the last fifteen years a major international research effort has been directed at developing effective vaccines and therapies for AIDS but has so far only achieved very limited success. AIDS is a disease which results from chronic infection by Human Immunodeficiency Virus (HIV). At least ten million people worldwide and at least one million people in the USA are infected with HIV. It is widely accepted that AIDS is caused by HIV but the precisely how HIV infection leads to AIDS is still a matter of active scientific investigation. Current research into developing a vaccine to prevent AIDS is based on attempting to increase immune responses to the HIV but has so far failed to produce an effective product. There are now many thousands publications which describe attempts to develop AIDS therapies and vaccines by stimulating the human immune system to recognise and destroy the virus. The main problem appears to be that antibodies and cytotoxic T cell responses stimulated by prototype vaccines fail to protect against either HIV infection or AIDS disease progression because of the rapid mutation rate of HIV.

A number of drugs have been developed for the treatment of AIDS (mainly anti-viral drugs with a similar mode of action to 3'-azido-3'-deoxythymidine, AZT), but none have been demonstrated to prevent the development of AIDS after HIV infection. The main problem is that HIV mutates rapidly leading to changes in the virally encoded proteins which are the target for antiviral drugs and drug resistance develops quickly.

Systemic lupus erythematosus (SLE) is a disease which is normally viewed as being completely unrelated to AIDS. SLE is an autoimmune disease and effects mainly women. Over half a million women in the USA suffer from mild to severe SLE. SLE is an autoimmune disease with many immunological abnormalities such as lymphadenopathy, hypergaminaglobulimemia, leukopenia, deposition of antigen-antibody complexes and autoantibodies resulting in chronic generalized connective tissue disorders ranging from mild to severe marked by skin eruptions, arthralgiia, arthritis, anemia, visceral lesions, neurologic manifestations, fever and other constitution symptoms. Symptoms fluctuate in intensity over many years and SLE is normally controlled with immunosuppressive drugs ranging from non-steroidal anti-inflammatory drugs to immunosuppressive steroids but there is no effective treatment. SLE may be the result of immune activation triggered by a retrovirus but no retrovirus has been identified which has been show to cause SLE. GB 9411534.2 filed by Holms R. D, on 8th Jun. 1994 discloses how HIV induces an autoimmune mechanism related to SLE which eventually leads to AIDS.

SUMMARY OF THE INVENTION

The present invention is based on selectively decreasing certain immune responses to HIV using peptides based on human proteins particularly a human protein called ezrin, providing a novel and non-obvious solution to the problem of the prevention and treatment of AIDS. A number of investigators have described autoimmunity related to HIV infection but have not established that HIV induced autoimmunity directly causes AIDS. The present invention is based on my discovery of the molecular mechanism of HIV induced autoimmunity which leads to AIDS and parallels between HIV induced disease and autoimmune disease such as systemic lupus erythematosus (SLE). The present invention provides for preparations which inhibit autoimmune processes which lead to AIDS and SLE by the induction certain types of immunosuppression or immune tolerance. GB 9411534.2 filed by Holms R. D, on 8th Jun. 1994 discloses therapies and vaccines for the treatment and prevention of AIDS based on this novel autoimmune mechanism induced by HIV.

I propose that just before the HIV epidemic commenced, HIV acquired a small piece of human DNA which allowed it to evolve a specific mechanism to replicate more efficiently by activating the human immune system. Unfortunately, HIV encoded derivatives of this human sequence not only activate the system but also induce autoimmunity and apoptosis. When a peptide derived from the virus, in a complex with certain types of MHC, is seen as sufficiently foreign to induce an immune response but has sufficient sequence homology with human peptides to trigger T cells which recognise both viral and human antigens, there is a serious risk of a chronic autoimmune response. This type of molecular mimicry has been postulated for the induction of a number of autoimmune diseases including multiple sclerosis. Mammalian immune systems also tend to be strongly activated by foreign antigenic peptides which are very similar but not the same as self antigens.

The HIV amino acid sequence;
$NH_2$ThrLysAlaLysArgArgValValGluArgGluLysArgCOOH
(SEQ ID NO. 1),
at position 498 to 510 (in the conserved C4 region) at the carboxy-terminus of HIV gp120 (a predicted alpha-helical region) is encoded between the direct repeats of a putative transposable element and appears to be a recent addition of human DNA to the virus. It is an immunodominant region of gp 120 in man and accounts for up to 70% of the total antibody response generated to the virus in some individuals although the antibodies are not virus-neutralising. A peptide derived from this region is also a dominant MHC Class-I restricted epitope for the induction of Cytotoxic T Lymphocytes (CTL). The sequence is conserved in all isolates of HIV-1 and HIV-2 against a background of a high mutation frequency (it is even more stable than the CD4 binding site) but it is different from an equivalent SIV sequence.

This 13 amino acid sequence of HIV;
$NH_2$ThrLysAlaLysArgArgValValGluArgGluLysArgCOOH
(SEQ ID NO. 1), is likely to be an epitope
for the induction of autoimmunity as it has a high degree of homology (50% or greater) with certain human sequences. I have named amino acid sequences in HIV which mimic human sequences; Virus Homologous Peptide (referred to hereinafter as VHP) and the above HIV amino acid sequence VHP1. I have named the group of human amino acid sequences derived from endogenous human protein sequences which the virus mimics, Human Endogenous Peptide (referred to hereinafter as HEP).

Although I propose the following novel immunological process to describe the mechanism of action of these human peptides (HEPs), the following immunological process serves to illustrate the invention only, and should not be construed as limiting it in any way.

I suggest that there is a positive selection mechanism for mutants of HIV which maintain the HIV sequence VHP1 ($NH_2$ThrLysAlaLysArgArgValValGluArgGluLysArg COOH)(SEQ ID NO. 1) at position 498 to 510 (conserved C4 region) at the C-terminus of HIV gp120. This sequence is maintained because when it is presented by some MHC Class I molecules (particularly MHC Class I B8 and MHC Class I B35) and most MHC Class II DR molecules, it is important for inducing large numbers of activated T cells in which HIV infection and replication occurs. Unfortunately, the activated CD4+ T cells die or are killed rapidly after VHP1 activation and a population of VHP1 activated CD8+ T cells raise the level of autoreactive responses. Eventually the combination of both immunological processes leads to AIDS.

Chronic HIV infection results in continuous presentation of VHP1 produced by HIV and continuous stimulation of the immune system. Although the presence of activated of T cells is essential for HIV replication, HIV only infects and kills a small minority of the VHP1 activated T cells. The majority of the activated T cells die as a result of VHP1 over stimulation or are destroyed by negative feedback mechanisms in the immune system involving autoreactive T cells. T cells are continually produced by the body to make good these losses in a chronically infected HIV patient but the net result is a progressive decline in CD4+ T cells over a number of years.

I also propose that the continuous presentation of VHP peptide by certain MHC Class I molecules of HIV infected cells breaks the tolerance of the host immune system to self peptides such as those derived from ezrin and other HEPs presented on activated T and B cells. The general level of activation leads to the stimulation of autoreactive cytotoxic T cells and chronic B cell activation with the over production of a range of antibody molecules including autoreactive antibody. A key step in the activation of the autoimmune process in HIV infected individuals is the stimulation of autoreactive CD8+ cells which carry cross reactive T cell Receptor (TCR) molecules that recognise both VHP and HEP.

It is an object of this invention to prevent and treat AIDS and SLE and related disorders by the induction of specific immunological tolerance which inhibits the above pathological mechanism. It is an object of the invention to provide composition of matter comprising pharmaceutical grade purified peptide or a mixture of two or more different peptides up to thirty amino acids long or derivative molecules with additional chemical groups attached to such peptides, comprising an amino acid sequence with at least 50% homology over fourteen consecutive amino acids with the following human amino acid sequence:
NH$_2$ThrGluLysLysArgArgGluThrValGluArgGluLysGlu COOH(SEQ ID NO. 2),
(the fourteen amino acid sequence hereinafter referred to as HEP1) and a purified peptide or mixture of two or more different peptides up to thirty amino acids long or derivative molecules with additional chemical groups attached to such peptides, comprising an amino acid sequence of at least five consecutive amino acids with 100% homology with HEP1. It is a purified object to provide a purified peptide comprising an amino acid sequence sufficiently duplicative of the fourteen amino acid sequence HEP1. It is a further object of the invention to provide a preparation of comprising peptides and peptide derivatives with at least 50% homology over fourteen consecutive amino acids with HEP1 and a purified peptide or mixture of two or more different peptides up to thirty amino acids long or derivative molecules with additional chemical groups attached to such peptides, comprising an amino acid sequence of at least five consecutive amino acids with 100% homology with HEP1, for the prevention and treatment of AIDS and related disorders which inhibits in vivo in man, partially or completely, HIV virus as measured by either an HIV p24 antigen assay in vitro or by an HIV infectivity assay in vitro. It is a further object of this invention to provide a preparation comprising peptides and peptide derivatives with at least 50% homology over fourteen consecutive amino acids with HEP1 and a purified peptide or mixture of two or more different peptides up to thirty amino acids long or derivative molecules with additional chemical groups attached to such peptides, comprising an amino acid sequence of at least five consecutive amino acids with 100% homology with HEP1, for the prevention and treatment of AIDS and related disorders, and for the prevention and treatment of Systemic Lupus Erythematosus and related disorders, which inhibits in vivo in man , partially or completely, autoimmune or autoreactive responses measured in vitro in a T cell Proliferation Assay.

Figure 1:
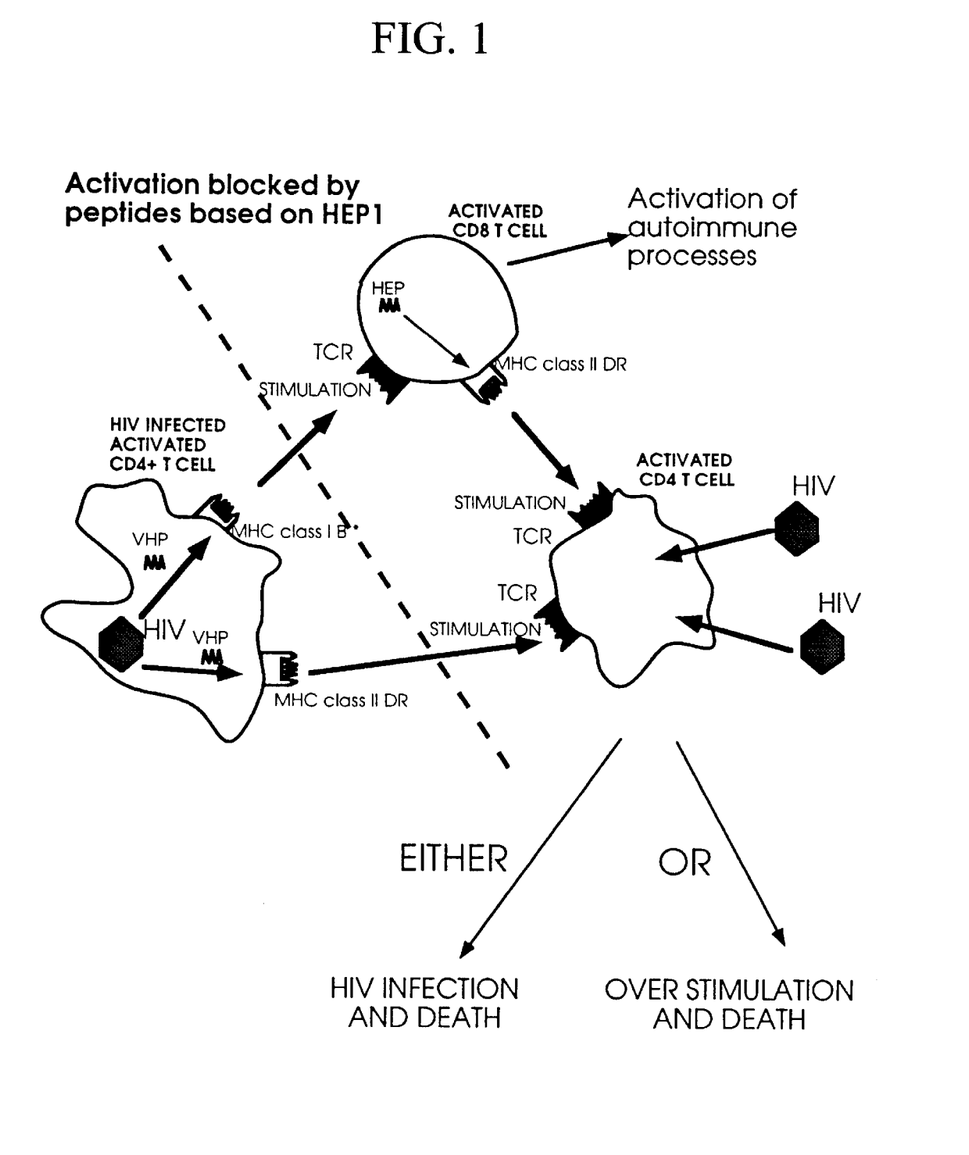
FIG. 1 entitled 'Immune activation and HIV infection' is a schematic diagram to show how an HIV infected CD4+ cell activates other CD4+ and CD8+ cells by the presentation of VHP on MHC molecules. The minority of CD4+ cells activated by this process are then infected by HIV while the majority of CD4+ T cells become over stimulated and die.

The close similarity between foreign VHP1 and self HEP1 when presented by certain MHC molecules and the possible immunoregulatory role of HEP1 in the healthy immune system, leads to strong stimulatory signals being transmitted through the immune system during HIV infection. The administration of HEP1 above the threshold for immunological tolerance induction is likely to block the VHP1 mediated activation of the immune system by HIV infected T cells. The clinical result of HEP1 administration predicted from the above model of HIV induced autoimmunity is lower levels of immune activation, a rise in CD4 T cell levels and a fall in the level of chronic HIV infection. (FIG. 1)

BRIEF DESCRIPTION OF THE DRAWINGS

Some of the activated CD8+ T cells are autoreactive and activate an autoimmune process which kills or suppresses activated T cells expressing HEP. The administration of HEP1 blocks the HIV induced T cell activation process and inhibits chronic HIV infection.

BRIEF DESCRIPTION OF THE SEQUENCES

SEQ ID NO. 1 is an amino acid sequence of a peptide according to the present invention.

SEQ ID NO. 2 is an amino acid sequence of a peptide according to the present invention.

SEQ ID NO. 3 is an amino acid sequence of a peptide according to the present invention.

DETAILED DESCRIPTION OF THE INVENTION

Induction of immune tolerance with HEP1 related peptides and the prevention and treatment of AIDS The non-obvious similarities between the HIV amino acid sequence;

NH₂ThrLysAlaLysArgArgValValGluArgGluLysArgCOOH (SEQ ID NO. 1), position 498 to 510 (conserved C4 region) at the C-terminus of HIV gp120 (VHP1) and sequences in human proteins, were investigated using computer searches of the SwissProt protein sequences database (Release 25). 1 established that VHP1 has a 70% sequence homology to an evolutionarily conserved human protein called ezrin between amino-acid positions 324–337 of ezrin. The result of the search for homology is set forth in the table below.

In addition to Ezrin, other human (self) proteins also possess a weaker primary sequence homology with VHP1: these include Heat shock protein 89, NK-TR protein, T complex protein, Adrenergic receptor Type 2, Creatine Kinase, Trypsin inhibitor, Aldehyde Dehydrogenase, Opioid Receptor (kappa), Glycine Receptor (Alpha-2 chain) and Ryanodine receptor. Mouse Histone H2B (very similar to human Histone H2B) also has homology.

It is an object of this invention that induction of tolerance can be used to switch-off immune activation and autoimmunity induced by HIV to prevent and treat HIV infection and AIDS. The present invention provides a vaccine against AIDS comprising a toleragenic dose (significantly larger than the threshhold dose sufficient to stimulate an immune response) of pharmaceutical grade purified peptide or a mixture of two or more different peptides up to thirty amino acids long or derivative molecules with additional chemical

|  |  |  |  |  |  |  | HIV | gp120-gp41 |  | Cleavage site-X |  |  |  |
|---|---|---|---|---|---|---|---|---|---|---|---|---|---|
| Position | 498 | 499 | 500 | 501 | 502 | 503 | 504 |  | 505 | 506 | 507 | 508 | 509 | 510 |
| gp120 | Thr | Lys | Ala | Lys | Arg | Arg | Val |  | Val | Glu | Arg | Glu | Lys | Arg |
| Homology | \| |  | \| | \| | \| | \| |  |  | \| | \| | \| | \| | \| |
| Ezrin | Thr | Glu | Lys | Lys | Arg | Arg | Glu | Thr | Val | Glu | Arg | Glu | Lys | Glu |
| Position | 324 | 325 | 326 | 327 | 328 | 329 | 330 | 331 | 332 | 333 | 334 | 335 | 336 | 337 |

I made the unexpected discovery that nine out of fourteen amino acids were identical when the HIV amino acid sequence between position 498 and 510 of gp120 was compared to the human amino acid sequence between positions 324 and 337 of ezrin. It is not obvious from prior publications that this region ezrin is important for immune regulation.

The fourteen amino acid sequence of HEP1,

NH₂ThrGluLysLysArgArgGluThrValGluArgGluLysGlu COOH(SEQ ID NO. 2), is identical to the amino acid sequence between positions 324 and 337 of human ezrin. No publication had disclosed HEP1 related peptides in man.

Ezrin, a human tubulin binding protein, is found in the cytoplasm of T cells and is phosphorylated by tyrosine kinase during T cell activation. Ezrin is also known as P81, Cytovillin or Villin-2, is a protein of 585 amino acids. The homology extends over a predicted alpha-helical region of ezrin and is adjacent to the tyrosine 353 propoxylation site. Ezrin is part of a family of ezrin related proteins, which includes ezrin, radixin, moesin and merlin. All these proteins are related in the region that shows similarity to gp120, but ezrin has the most significant homology with 9/13 identities. Although ezrin behaves as a soluble protein in T cells and appears to be diffusely cytoplasmic by immunofluorescence staining, it is believed that the critical population of ezrin is that which is associated with the submembraneous cortical cytoskeleton (Identification of Ezrin as an 81-kDa Tyrosine-phosphorylated protein in T cells Egerton M., Burgess W. H., Chen D., Druker B. J., Bretscher A., Samelson L. E.*The Journal of Immunology* 1992 149: 1847–1852). It may also be important for the autoimmune pathology of AIDS that ezrin is also found localized to microvillar actin microfilament cores in the brush border of the intestinal epithelium and also in neurons. In the gut epithelium ezrin is involved in changes in cell membrane morphology in response to stimulation (Identification of the Two Major Epidermal Growth factor-induced Tyrosine Phosphorylation Sites in the Microvillar Core Protein Ezrin, Krieg J., Hunter T.,*Journal of Biological Chemistry* 1992 267: 19258-19265).

groups attached to such peptides, comprising an amino acid sequence with at least 50% homology over fourteen consecutive amino acids with HEP1 and a purified peptide or mixture of two or more different peptides up to thirty amino acids long or derivative molecules with additional chemical groups attached to such peptides, comprising an amino acid sequence of at least five consecutive amino acids with 100% homology with HEP1 or any combination thereof, or peptides similar thereto. The prefered route of administration is oral, although it is equally possible to achieve tolerance by sub-cutaneous, intravenous or intramuscular administration by standard methods. It is an aspect of this invention that a peptide vaccine based on HEP1 can be administered to prevent and treat AIDS in HIV infected people by the induction of tolerance to the VHP sequences. It is another aspect of this invention that a peptide vaccine based on HEP1 can be administered to prevent and treat SLE in people by the induction of tolerance to other HEP sequences.

HOW TO MAKE

Peptides used for the toleragenic vaccine may be synthesized, for example, using a solid phase method using either Boc or Fmoc chemistry or any other practical route for peptide synthesis known to those skilled in the art of peptide synthesis. After synthesis, peptides are cleaved from the resin (in solid phase methods) and deprotected using trifluoromethane sulphonic acid or Hydrogen Fluoride or other agents. Peptides may be desalted by column chromatography and purified by HPLC. Purity of the peptides may be demonstrated by reverse-phase HPLC or by automatic sequencing. Without limiting peptide or peptides either dissolved in sterile pharmaceutical saline or distilled water to a final concentation between 1 and 1000 mg/ml. The preparation may be freshly made up for each administration or may be stored frozen for up to 30 days at −20° C. (see EXAMPLE 1 & EXAMPLE 2).

HOW TO USE

The induction of immunological tolerance by oral administration or sub cutaneous administration of peptide solutions has been successfully achieved in various animal experiments. The immunological tolerance induced by peptides can occur either by induction of T cell anergy (direct inhibition) or by induction of suppressor T cell populations (indirect inhibition) by the peptides. Those skilled in the art of induction of immunological tolerance are aware of procedures to induce tolerance in animals by oral, subcutaneous, intravenous or intramuscular administration of small peptides derived from cross reactive antigens. Examples of these procedures have been disclosed in the following publications:

Could specific oral tolerance be a therapy for autoimmune disease, Stephen H., Thompson G., Staines N.A *Immunol. Today* 1990 11: 396–399

Induction of immunity and oral tolerance with polymorphic class II major histocompatibility complex allopeptides in the rat, Sayegh M. H., Khoury S. J., Hancock W. W., Weiner H. L., Carpenter C. B. *Proc Natl Acad Sci* USA 1992 89: 7762–7766

Oral tolerance in experimental autoimmune encephalomyelitis, Whitacre C C, Gienapp I. E., Orosz C. G.,Bitar D. M., *The Journal of Immunology* 1991 147 2155–2163

Prevention of experimental autoimmune myasthenia gravis by manipulation of the immune network with a complementary peptide for the acetylcholine receptor, Araga S., LeBoeuf R. D., Blalock J. E. *Proc Natl Acad Sci* 1993 90: 8747–8751

Peripheral T-cell tolerance induced in naive and primed mice by subcutaneous injection of peptides from the major cat allergen FeldI, Briner T. J., KuoM., Keating K. M., Rogers B. L., Greenstein J. L., *Proc Natl Acad Sci* 1993 90 7608–7612

Two factors are important for the induction of tolerance: high dose of soluble peptide antigen and absence of any co-stimulatory particles or adjuvant. Generally, immunological activation occurs with very much lower doses of peptide antigen than the threshhold dose above which the peptide antigen induces tolerance or inhibition of immune responses (for example in man a very small dose of 10 nanograms of a small foreign peptide antigen may illicite a strong immune response whereas a 10 milligram dose may inhibit the immune response). The dose range for the induction of tolerance varies between peptides but the amount or concentration may be determined experimentally. Subcutaneous administration of peptides yield final serum concentrations of peptide between 50–100× higher than by the oral route and therefore tolerance may be achieved with less peptide than by the oral route. The peptide solution should be filter sterilised to remove particulates and any microbiological contaminants, if a peptide solution is to be administered by injection.

It is an object of this invention that the preferred doses are between 1 mg and 5000 mg of pharmaceutical grade purified peptide or a mixture of two or more different peptides up to thirty amino acids long or derivative molecules with additional chemical groups attached to such peptides, comprising an amino acid sequence with at least 50% homology over fourteen consecutive amino acids with HEP1 and a purified peptide or mixture of two or more different peptides up to thirty amino acids long or derivative molecules with additional chemical groups attached to such peptides, comprising an amino acid sequence of at least five consecutive amino acids with 100% homology with HEP1 or any combination thereof, peptides similar thereto.

Although it is theoretically possible to attempt to induce immunological tolerance with peptides based on any HIV amino acid sequence, there is the general risk that a protective immune response against HIV may be inhibited. There is also a specific risk associated with administering peptides based on VHP1 to induce immunological tolerance as an incorrect dose of VHP1 based peptides may aggravate the disease by increasing immune activation. It is an advantage of this invention that the administration of peptides based on human amino acid sequences are likely to be significantly safer than peptides based on HIV amino acid sequences.

The following Examples serve to illustrate the invention only, and should not be construed as limiting it in any way.

EXAMPLE 1

IN VITRO MODEL OF VHP1-INDUCED AUTOIMMUNITY IN HUMAN CELLS FROM UNINFECTED DONORS.

MATERIALS and METHODS

Peptide synthesis

VHP1 peptide and control peptide used in this study were synthesized using a solid phase method using Fmoc chemistry. They were cleaved from the resin and deprotected using trifluoromethane sulphonic acid. Peptides were desalted on a P-10 column in PBS (pH 7.3). Homogeneity of the peptides was indicated by reverse-phase HPLC. Peptides were sequenced by automatic Edman degradation using gas phase sequence and were shown to be >95% pure. The following peptides were synthesised:

13 amino acid sequence of VHP1 derived from HIV: NH$_2$ThrLysAlaLysArgArgValValGluArgGIuLysArgCOOH (SEQ ID NO. 1)

A 14 amino acid control sequence: NH$_2$LeuGluAspArgArgAlaAlaValAspThrValCysArgAla COOH(SEQ ID NO. 3)

Donors

All donors who volunteered for this study were HIV negative. The MHC phenotype of donors was determined before the experiment. The number of the subtype of the A, B and C categories of MHC Class I phenotype and the number of the subtype of the DR, DP and DQ categories of MHC Class II phenotype of each donor is set out in the following tables:

| Donor | A | B | C | DR | DP | DQ |
|---|---|---|---|---|---|---|
| Donors positive for B8 or B35 (Trigger+) | | | | | | |
| FM | 1,3 | 8 | 7 | 3 | nd | nd |
| SW | 1,3 | 35,62 | nd | 1 | nd | 1 |
| WW | 11,36 | 35,61 | nd | 1 | nd | 1 |
| JMC | 1,2 | 8,45 | 6,7 | 3,4 | nd | 2,7 |
| Target 1 | 1 | 8 | 7 | 3 | 3 | 2 |
| Target 2 | 31 | 35 | 4 | 4 | nd | 7 |
| Donors negative for B8 or B35 (Trigger−) | | | | | | |
| TM | 3,28 | 7,14 | nd | 6 | nd | nd |
| JF | 2 | 17 | 3 | 6 | nd | 1 |
| KB | 1 | 7,14 | 7 | 4,11 | nd | 7 |
| ML | 2 | 44,52 | 5 | 2 | nd | 1 |
| Target 3 | 3 | 27 | 1 | 1 | nd | 5 |

Generation of VHP1 induced short-term cultures

Peripheral Blood Mononuclear Cells (PBMC) were isolated from 8 HIV seronegative individuals who volunteered as donors for the study. Four donors FM, SW, WW, JMC (Trigger+) were positive for either MHC B35 or B8 and four donors TM, JF, KB, ML (Trigger−) were negative for MHC B35 or B8. PBMC (10$^6$/ml) from the each of the donors were incubated in the presence of VHP1 or control peptide at 100 ng/ml for 4–8 hours to produce Effector Cells. Irradiated autologous PBMC without VHP1 stimulation served as controls.

Cytotoxicity Assay

VHP1 induced short-term cultures of autoreactive T cells (Effector Cells) were assayed for cytotoxic activity against autologous PHA T cell blasts stimulated with 5 µg/ml PHA for 4–5 days at a concentration of $10^4$ cells/well in the absence of either control or VHP1 peptide (Target Cells). $1-2\times10^6$ Target Cells were labeled with 250 mCi of $^{51}$Cr in 0.3 ml of medium for 1 hour at 37° C. Target cells were washed 3× in medium, diluted to $10^5$ or $10^4$ cells/ml and 100 ml of cell suspension added to each well of a V-bottomed 96-well microtitre plate. Effector Cells were added to the Target Cells at Effector:Target (E:T) ratios from 50:1 to 6.25:1. Cultures were incubated for 4 hours at 37° C. and supernatants were harvested and counted for $^{51}$Cr release. Percent cytotoxicity is calculated using the formula : 100− (experimental release−spontaneous release)/(maximum release−spontaneous release). Spontaneous release and maximum release were determined by incubating target cells in medium or 1.0% Triton x−100 respectively. Results where calculated as means ± Standard Deviations (SD) of triplicate cultures and a positive result was scored above 20% specific lysis. The cytotoxicity assay was repeated for allogeneic Target cells from donors (Target-1, Target-2 and Target-3) and the percent specific lysis scored at an Effector:Target ratio of 10:1.

T cell Proliferation Assay

The proliferation assays was performed by culturing either PBMC or T cell lines ($10^4$ cells/well) in U-bottomed 96-well microtitre plates for 3 days at 37° C. stimulated with fresh irradiated autologous PBMC and r-IL2 either with or without 1 µM VHP1. PBMC or T cell lines were rested in the absence of r-IL2 for 24 hours prior to assay. Three positive control cultures of the PBMC or T cell lines were stimulated with 10 µg/ml PHA, 10 µg/ml PPD and 0.1 µg/ml SEB (Staph. Enterotoxin) respectively to determine maximum proliferation. The two negative controls were an unstimulated culture of PBMC or T cell line and irradiated PBMC or T cell line under the same conditions. During the final 6 hours before harvesting, the cultures received 1 mCu/well of [$^3$H] thymidine. The cells were harvested onto glass fibre filters by a semiautomatic harvester and the incorporation of labeled thymidine was quantitated by liquid scintillation spectrometry. The results are expressed as counts per minute (cpm) of the mean for triplicate cultures.

RESULTS

Induction of autoreactive cells by VHP1

Short term cultures of PBMC from donors positive for B8 or B35 (trigger+) stimulated with VHP1 produced Effectors which showed significant autocytoxic responses against activated autologous T cell targets in the Cr release cytoxicity assays. Short term cultures of PBMC from donors positive for B8 or B35 stimulated with control peptide (Control) and short term cultures of PBMC from donors negative for B8 or B35 (trigger−) did not produce significant levels these autocytotoxic Effectors. The dependence of autocytotoxic responses on MHC phenotype of uninfected donors in short term cultures of PBMC stimulated with VHP1 is shown below.

Dependence of autoreactive response to VHP1 on MHC Phenotype of Donor

|  | Peptide stimulant | |
|---|---|---|
| DONOR | VHP1 | Control |
| Trigger+ | | |
| FM | + | − |
| SW | + | − |
| WW | + | − |
| JMC | + | − |
| Trigger− | | |
| TM | − | − |
| JF | − | − |
| KB | − | − |
| ML | − | − |

Identification of the Target of VHP1 Induced Autoreactive Cells

To establish the MHC specificity of the cytotoxic cells stimulated by VHP1, further Cytotoxicity Assays with allogeneic PHA activated T cell Targets with different MHC phenotypes were then performed. The Effectors were derived from short term cultures of PBMC from donors of either MHC B8 or B35 (trigger+) incubated with VHP1 for 4–8 hours. The Target Cells were from donors with either B8 B35 (trigger+) or B27(Trigger−) MHC phenotype. Target PBMC incubated with radioactive $^{51}$Cr for one hour before being mixed with Effectors. Effector Cells were mixed with radiolabelled Target Cells and incubated for 4 hours and lysis was measured by release of radioactive $^{51}$Cr.

| Donor | MHC Phenotype | Predicted Sensitivity to AIDS |
|---|---|---|
| EFFECTORS | | |
| JMC | B8 | High |
| WW | B35 | High |
| SW | B35 | High |
| TARGETS | | |
| 1 | B8 | High |
| 2 | B35 | High |
| 3 | B27 | Low |

The measurement of percent specific lysis by $^{51}$Cr release at an Effector to Target Ratio of 10:1.

| Targets | Effectors (Donor-MHC) | | |
|---|---|---|---|
| (Donor-MHC) | JMC-B8 | WW-B35 | SW-B35 |
| Target1-B8 | 30 | 30 | 9 |
| Target2-B35 | 30 | 32 | 10 |
| Target3-B27 | 7 | 14 | 2 |

JMC-B8 Effectors efficiently hit both B8 and B35 Targets but not B27 Targets. WW-B35 Effectors efficiently hit both B8 and B35 Targets but not B27 Targets (the same specificity as the JMC-B8 Effectors). SW-B35 Effectors showed a similar pattern of specificity in that they recognised both B8 and B35 Targets but not B27 Targets but the overall cytotoxic activity from this donor was lower.

B8 and B35 both have the identical trigger amino acid sequence in the alpha-one domain of MHC Class I whereas B27 has a different sequence.(GB 9411534.2 filed by Holms R. D, on 8th Jun. 1994). B8 and B35 phenotypes have been associated with high sensitivity to the development of AIDS alter HIV infection in a number of clinical studies. I conclude that VHP1 is presented by MHC Class I B8 and B35 to Effector T cells in the short term cultures of PBMCs. I also conclude that the TCR of B8 and B35 Effector T cells are recognising a common epitope on MHC Class I B8 and B35 of the Targets which is absent on MHC Class I B27. The common epitope is likely to be a combination of the common MHC Class I B trigger sequence (present in the alpha one domain of both B8 and B35 but not on B27) plus human peptides resembling HEP1 (self peptides homologous to VHP1).

An autoreactive T cell line was established from donor WW (HLA-B35 phenotype) by stimulation with VHP1. The line was a mixed population of 59% CD4+T cells and 28% CD8+T cells. A proliferation assay was performed to measure to level of proliferation in the T cell line to autologous (self) cells. T cell line WW responded vigorously to autoantigens presented on autologous irradiated PBMC at similar levels to the PHA or PPD stimulated positive control cultures.

Discussion

I conclude that VHP1 (at low concentrations) activates the immune system and induces significant levels of autocytotoxic cells in donors with MHC phenotypes associated with sensitivity to developing AIDS rapidly (B8 or B35) while it is not so active in donors who do not carry the MHC phenotypes associated with sensitivity to rapid development of AIDS. The correlation between VHP1 sensitivity and sensitivity to rapid development of AIDS suggests that the expression and correct presentation of the VHP1 sequence in HIV infected people may be an important step in the disease process which leads to AIDS.

EXAMPLE 2

CLINICAL TRIAL OF HEP1 IN AN HIV INFECTED PATIENT

The objective of this study was to determine in an HIV infected patient if the induction of immunological tolerance to HEP1 could reduce immune activation and HIV infection. The design of the first clinical experiment was to orally administer HEP1 to the patient in daily 10 mg doses (the lower end of the preferred dose range). This was then followed approximately three months later with a subcutaneous administration of HEP1 at a higher dose of 140 mg. To assess the therapeutic benefit of HEP1, the following disease progression markers were measured by taking blood samples before, during and after each trial and determining: HIV levels by a p24 antigen assay, HIV infectivity by a cellular TCID assay and immune activation by quantitating levels of various lymphocytes.

The Patient

Patient PP volunteered to take peptide HEP1 orally while attending the HIV Clinic at Ealing Hospital NHS Trust. Patient PP is a white male, 32 years old and has been HIV infected for eight years and entered the trail with a T cell count of 80 cells / mm$^3$. He had not taken any anti-viral therapy (for example AZT) in the previous five years before the trial. At the time of the trial, the patient was HCV negative (Abbott 2nd generation), HepB negative and Blood group A rhesus (D) positive.

Synthesis of HEP1 peptide

Abbreviations

DCC—Dicyclohexylcarbodiimide
DIC—Diisopropylcarbodiimide
DCM—Dichloromethane
DMF—Dimethylformamide
TFA—Trifluoroacetic acid
Boc—t-Butlyoxycarbonyl-
HOBT—Hydroxybenzotriazole
DIEA—Diisopropylethylamine
DCU—Dicyclohexylurea
HF—Hydrogen Fluoride 370 mg of HEP1 (a 14 amino acid peptide) was synthesized by Boc-synthesis based on a human ezrin sequence: NH2ThrGluLysLysArgArgGluThrValGluArgGluLysGlu COOH (SEQ ID NO. 2). 0.05 mmole resin (Boc-aminoacid -OCH$_2$ pam resin) and a three fold excess of activated Boc-aminoacid solution (activated with 0.5M HBTU in DMF and 2.5 mmole DIEA) were coupled in the following steps. The resin was washed with DMF, Boc protecting groups removed with 100% TFA, the reaction was drained, flow washed with DMF for one minute, drained, activated amino acid solution was added, shaken for 10 minutes at room temperature then washed and the sequence of steps repeated for the next amino acid. On completion of the synthesis, the reaction mixture was flow washed with DMF, then with DCM and dried. The peptide was then cleaved from the resin with HF (−5° C. for 1.5 hours), the HF was evaporated, the mixture was washed with 5 ml ether and evaporated then the peptide dissolved in 6M guanidine 0.1M TRIS for HPLC preparative separation. After separation, the peptide was analysed for purity by HPLC and was determined to be over 99% pure HEP1. The peptide solution was then evaporated to a pure white fluffy solid under vacuum.

Preparation of HEP1 peptide for Oral Administration.

To a vial containing 221 mg of pure freeze dried HEP1 peptide approximately 5 ml of sterile distilled water was added to dissolve the peptide and the solution was washed into a 50 ml volumetric flask and made up to exactly 50 ml in the volumetric flask with more sterile distilled water giving a final concentration of 4.42 mg/ml HEP1. 2.26 ml volumes of the solution were transferred into twenty two separate lots in 5 ml plastic tubes and stored at −20° C. (10 mg of peptide per tube). Two vials were stored at −70° C. as reference solutions at the clinic and the remaining 20 vials were provided to the patient on dry ice in a vacuum flask. The vials were stored until use by the patient in a freezer at −20° C. The patient thawed out one tube (leaving the remaining tubes frozen in the Freezer) each morning and swallowed the solution one hour before breakfast. The procedure was repeated for twenty days.

Preparation of HEP1 peptide for Subcutaneous Administration.

HEP1 was administered subcutaneously to patient PP three months after the end of the oral administration study.

Preparation

To a vial containing 147 mg of pure freeze dried HEP1 peptide (no inorganic salts added) 1 ml of sterile distilled water was added to the vial to dissolve the peptide giving a final concentration of 147 mg/ml HEP1. The solution was filter sterilised through a 0.2 micrometer sartorius filter attached to a steril 5 ml syringe and then transfered a 5 ml sterile container.

Cellular TCID Assay

Cellular TCID is a technique that measures the relative amount of viral load within cells. Within four hours of a sample being taken from the HIV infected patient, 10$^6$ viable PBMC from the sample were obtained by centrifugation of the anticoagulated blood over Ficoll-Hypaque lymphocyte separation medium. A serial dilution of the patients cells was set up in a 24 well plate in decreasing amounts (1:1, 1:4, 1:16, 1:64 and 1:256 and a negative control using 0.9 ml special media (RPMI-1640) supplemented with 15% fetal calf serum and 10% interleukin 2. Infected cells were then cocultivated with $10^6$ PBMC derived from an uninfected human donor that had been stimulated for 24–48 hours with phytohaemagglutin (PHA) to activate the cells to make them susceptible to infection by HIV. The cocultures were subsequently monitored for the presence of p24 antigen in the supernatant fluid twice weekly for up to 14 days, during this period the plates were spun on days 4,7,11 and 14 and then a 50% medium change was performed. The medium was removed at days 7 and 14 and saved in duplicate 0.5 ml eppendorff tubes (minimum 250 μl/tube) for future p24 antigen testing. The medium was removed on day 11 and any remaining medium from day 14 (after saving for p24 antigen testing) was pooled and stored in liquid nitrogen for future Virus culture. A culture was considered positive if the concentration of p24 antigen in the supernatant on day 7 and day 14 exceeded 30 picogram/ml (typical cut-off value). The lowest number of peripheral mononuclear cells required to produce a positive culture was taken as the end point and the reciprocal of the end point dilution indicated the relative number of infected cells in the patient.

p24Ag Assay p24Ag is a marker of HIV infection as well as a predictor of HIV disease progression. The p24Ag assay measures p24 antigen from the core of HIV and is an immunoassay using murine monoclonal antibody coated onto microwell strips. The assay detects HIV in plasma, serum or tissue culture medium. If present, the antigen binds to the antibody-coated microwells. The bound antigen is recognised by biotinylated antibodies to HIV which react with conjugated strepavidin-horseradish peroxidase. Colour develops from the reaction of the peroxidase with hydrogen peroxidase in the presence of tetramethylbenzidine (TMB) substrate. Specimens which are HIV p24Ag positive can be quantitated by setting up a standard curve using serial dilutions of the Antigen Reagent. The assay is not accurate below 30 picograms per ml.

CD4, CD8, NK

T cell subsets were measured by adding a whole blood sample to a 4.5 ml tube containing EDTA and staining with monoclonal antibodies to CD3, CD4 and CD8. The percentage of T cells in Peripheral Blood Lymphocytes were determined by flow-cytometric procedures. The numbers of CD4 and CD8 T cells were determined by obtaining total and differential white-cell counts and multiplying by the appropriate factor obtained on flow cytometry.

Results: Oral Administration of HEP1

Blood samples were taken from the patient 69 days before the trial and on the first day of the trial before the first dose of HEP1, to determine the background levels of the disease progression markers. Oral administration of HEP1 solution containing 10 mg HEP1 was started on day 2 of the trial and continued until day 22. Further Blood samples were taken for analysis on day 7, day 14, day 21 and day 28 of the trial (7 days after the last dose of HEP1). The patient experienced no adverse reactions and continued to feel well through out the administration of HEP1.

The following markers of HIV disease progression were assayed: p24Ag (the concentration of HIV p24 protein in picogram/ml in the blood), TCID (the infectivity of the HIV in the cells of blood sample measured by an in vitro cell culture assay in which a serial dilution of the sample was mixed with activated uninfected PBMC and the level of HIV infection determined by p24Ag assay), total white count (immune activation measured by the number of white cells per $mm^3$), CD4 (the number of CD4 positive cells per $mm^3$), CD8 (the number of CD8 positive cells per $mm^3$), NK (the number of Natural Killer cells per $mm^3$), Lymphocytes (the number of cells per $mm^3$), Monocytes (the number of cells per $mm^3$), and Granulocytes (the number of cells per $mm^3$). Normalised data was calculated by dividing each data point by the value of its data series on day 1 of the trail and multiplying by 100.

| | BEFORE TREATMENT | | DURING TREATMENT | | | AFTER |
|---|---|---|---|---|---|---|
| Trial day | day-69 | day 1 | day 7 | day 14 | day 21 | day 28 |
| Date | 3/11/94 | 10/1/95 | 17/1/95 | 24/1/95 | 1/2/95 | 7/2/95 |
| p24Ag | n/a | 71 | 44 | n/a | n/a | 38 |
| TCID | n/a | 1:16 | n/a | n/a | n/a | 1:1 |
| White count | 7900 | 8200 | 8200 | 7700 | 6800 | 5500 |
| CD4 | 90 | 80 | 80 | 90 | 80 | 80 |
| CD8 | 850 | 900 | 850 | 900 | 910 | 730 |
| NK | 20 | 30 | 30 | 40 | 40 | 20 |
| Lymphocytes | 1260 | 1480 | 1150 | 1460 | 1160 | 1050 |
| Monocytes | 630 | 570 | 490 | 620 | 540 | 440 |
| Granulocytes | 6000 | 6230 | 6560 | 5620 | 5100 | 4020 |
| % Lymphocytes | 15.4 | 17.8 | 15.5 | 16.8 | 18.6 | 20 |
| % Monocytes | 4.2 | 6.1 | 3.1 | 6.4 | 5.2 | 5.5 |
| % Granulocytes | 80.4 | 76.1 | 81.4 | 76.8 | 76.2 | 74.5 |

NORMALISED DATA- day 1 = 100

| Trial day | day-69 | day 1 | day 7 | day 14 | day 21 | day 28 |
|---|---|---|---|---|---|---|
| Date | 3/11/94 | 10/1/95 | 17/1/95 | 24/1/95 | 1/2/95 | 7/2/95 |
| p24Ag | | 100 | 62 | | | 54 |
| TCID | | 100 | | | | 6 |
| White count | 96 | 100 | 100 | 94 | 83 | 67 |
| CD4 | 113 | 100 | 100 | 113 | 100 | 100 |
| CD8 | 94 | 100 | 94 | 100 | 101 | 81 |
| NK | 67 | 100 | 100 | 133 | 133 | 67 |
| Lymphocytes | 85 | 100 | 78 | 99 | 78 | 71 |
| Monocytes | 111 | 100 | 86 | 109 | 95 | 77 |
| Granulocytes | 96 | 10 | 105 | 90 | 82 | 65 |
| % Lymphocytes | 87 | 100 | 87 | 94 | 104 | 112 |
| % Monocytes | 96 | 100 | 51 | 105 | 85 | 90 |
| % Granulocytes | 106 | 100 | 107 | 101 | 100 | 98 |

Figure 2:
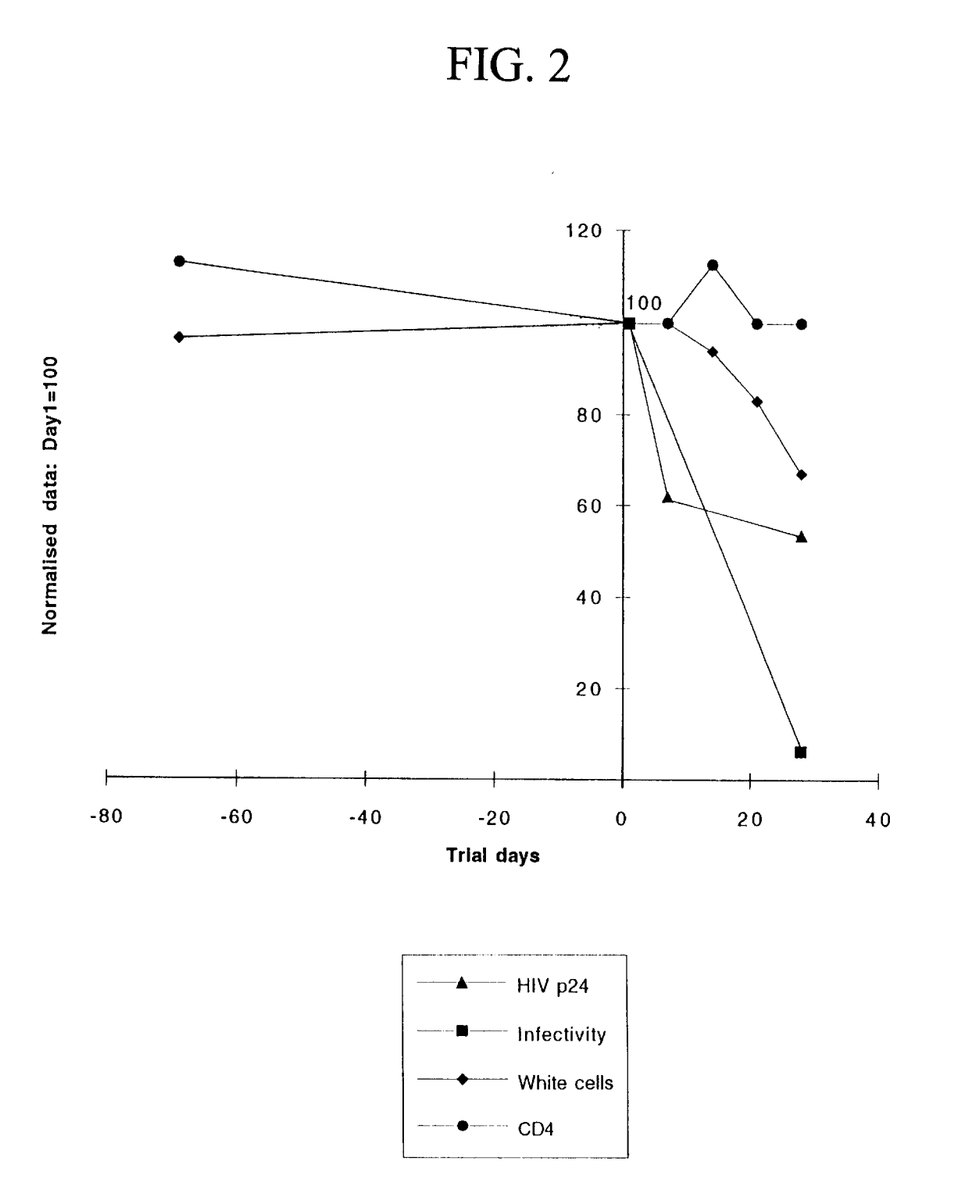
FIG. 2 entitled 'Inhibition of HIV by Orally Administered HEP1 in vivo in patient PP' is a graphical representation of the normalised clinical trial data in Example 2 (data rebased to 100 on day 1 of the trial). The graph shows the result of oral administration of HEP1: the decline in HIV virus particles as measured by p24Ag levels, the decline in HIV infectivity as measured by a TCID assay and the fall in total white count (decline in immune activation).

These preliminary clinical results show that orally administered HEP1 reduced viral load by 46% as measured by p24Ag, and reduced the infectivity of HIV by 16 X as measured by TCID and that the effect persisted for 7 days after treatment. It is important to note that the p24Ag level was only just above background at 38 picogram/ml as 30 picogram/ml is considered the typical cut-off value. The total white cell count was rising before treatment but fell during and after treatment suggesting a reduction in immune activation had been achieved during treatment. The persistance of these effects for seven days after treatment suggests that a T suppressor cell population had been induced in the patient which reduced infectivity of HIV and immune activation. CD8 increased during treatment but there was no significant increase in CD4 count (at this concentration of HEP1). (FIG. 2)

Results

Subcutaneous Administration of HEP1

0.95 ml (the volume equivalent to 14 mg HEP1) of the steril solution was self-injected subcutaneously in the abdomental wall in one dose on day 1 of the subcutaneous HEP1 trial. Patient PP experienced a stinging sensation which lasted approximately 15 minutes but there were no other adverse reactions. Blood samples were taken on day–92, day–57, day–8, day 1 before the HEP1 injection and day 1

* four hours after the injection and then 6 days and 13 days after the HEP1 injection. The samples were assayed for p24, TCID, CD4, CD8, total white count, lymphocytes, granulocytes, monocytes and the data is set out in the table below (normalised data was calculated as described above).

|  | End Oral study | BEFORE TREATMENT | | | AFTER | |
|---|---|---|---|---|---|---|
| Trial day | day-91 | day-56 | day-7 | day 1 | day 1* | day 6 |
| Date | 7/2/95 | 14/3/95 | 2/5/95 | 9/5/95 | 10/5/95 | 16/5/95 |
| p24Ag | 38 | n/a | n/a | n/a | n/a | n/a |
| TCID | 1:1 | n/a | n/a | n/a | n/a | n/a |
| White count | 5500 | 6600 | 8200 | 5600 | 4600 | 5400 |
| CD4 | 80 | 75 | 70 | 80 | 120 | 80 |
| CD8 | 730 | 880 | 670 | 880 | 1130 | 780 |
| NK | 20 | 75 | 40 | 30 | 30 | |
| Lymphocytes | 1050 | 1250 | 980 | 1290 | 1520 | |
| Monocytes | 440 | 400 | 570 | 450 | 510 | |
| Granulocytes | 4020 | 4950 | 6640 | 3860 | 2530 | |
| % Lymphocytes | 20 | 19 | 12.9 | 23.3 | 33 | 22.2 |
| % Monocytes | 5.5 | 6 | 7 | 8 | 11 | |
| % Granulocytes | 74.5 | 75 | 81 | 69 | 55 | |

| NORMALISED DATA- day 1 = 100 | | | | | | |
|---|---|---|---|---|---|---|
| Trial day | day-91 | | | | | |
| Date | 7/2/95 | day-56 | day-7 | day 1 | day 1* | day 6 |
| p24Ag | n/m | n/a | n/a | n/a | n/a | n/a |
| TCID | n/m | n/a | n/a | n/a | n/a | n/a |
| White count | 98 | 118 | 146 | 100 | 82 | 96 |
| CD4 | 100 | 94 | 88 | 100 | 150 | 100 |
| CD8 | 83 | 100 | 76 | 100 | 128 | 89 |
| NK | 67 | 250 | 133 | 100 | 267 | |
| Lymphocytes | 81 | 97 | 76 | 100 | 118 | |
| Monocytes | 98 | 89 | 127 | 100 | 113 | |
| Granulocytes | 104 | 128 | 172 | 100 | 66 | |
| % Lymphocytes | 86 | 82 | 55 | 100 | 142 | |
| % Monocytes | 69 | 75 | 88 | 100 | 138 | |
| % Granulocytes | 108 | 109 | 117 | 100 | 80 | |

Figure 3:
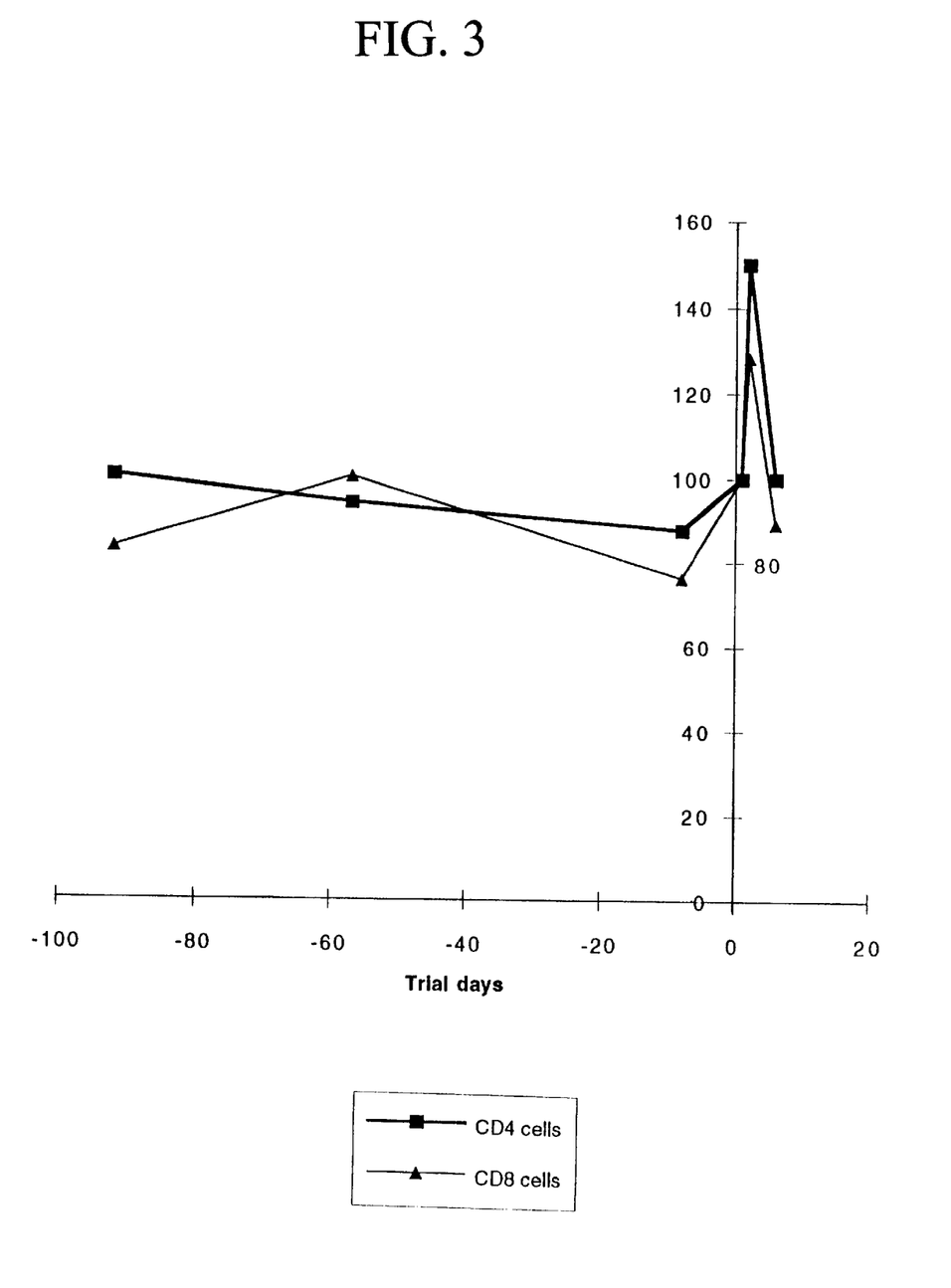
FIG. 3 entitled 'Improvement of Immune Status by Subcutaneously Administered HEP1 in vivo in patient PP' is a graphical representation of the normalised clinical trial data in Example 2 (data rebased to 100 on day 1 of the trial). The graph shows the result of subcutaneous administration of one larger dose of HEP1: a sharp increase in CD4+ and CD8+ T cells.

The subcutaneous administration of one larger dose of HEP1 resulted in a sharp rise in both CD4 T cells (+50%) and CD8 T cells (+28%) after the HEP1 injection followed by a return to the pre-injection i levels six days later (p24Ag and TCID data was not ready in time for the filing of the application). (FIG. 3)

---

What is claimed is:

1. A purified peptide consisting of the amino acid sequence:

ThrGluLysLysArgArgGluThrValGluArgGluLysGlu (SEQ ID NO. 2).

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Thr  Lys  Ala  Lys  Arg  Arg  Val  Val  Glu  Arg  Glu  Lys  Arg
1                 5                             10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Thr  Glu  Lys  Lys  Arg  Arg  Glu  Thr  Val  Glu  Arg  Glu  Lys  Glu
1                 5                             10
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear (ii) MOLECULE TYPE: peptide (xi) SEQUENCE DESCRIPTION: SEQ ID NO:3:

Leu Glu Asp Arg Arg Ala Ala Val Asp Thr Val Cys Arg Ala
1               5                   10